United States Patent [19]

Horii et al.

[11] 4,089,947

[45] May 16, 1978

[54] ANTIBIOTIC COMPOSITIONS CONTAINING VALIDAMYCIN COMPOUNDS

[75] Inventors: Satoshi Horii, Sakai; Yukihiko Kameda, Kanazawa; Takashi Iwasa, Kyoto; Hiroichi Yamamoto, Kobe, all of Japan

[73] Assignee: Takeda Chemical Industries Ltd., Osaka, Japan

[21] Appl. No.: 710,238

[22] Filed: Jul. 30, 1976

Related U.S. Application Data

[62] Division of Ser. No. 245,135, Apr. 18, 1972, Pat. No. 4,011,391.

[51] Int. Cl.$^2$ .................... A61K 31/71; C07H 15/20
[52] U.S. Cl. ......................... 424/181; 195/80 R; 536/17
[58] Field of Search .................... 424/181; 536/17

[56] References Cited

PUBLICATIONS

Iwasa et al., "The Journal of Antibiotics", vol. XXIII, No. 12, 1970, pp. 595–602.
Horii et al., "Chem. Abst.", vol. 76, 1972, p. 97891w.

*Primary Examiner*—Johnnie R. Brown
*Attorney, Agent, or Firm*—Wenderoth, Lind & Ponack

[57] ABSTRACT

Novel antibiotics, termed validamycins C, D, E and F, and acid salts thereof, are prepared by cultivating a validamycin-producing strain of microorganism of the genus Streptomyces, and optionally converting the free base to its acid salt. These antibiotics, as well as validoxylamines A and B, are useful for controlling plant diseases, and can be applied to the plants in the form of the cultured broth, filtrate or concentrate thereof, or purified preparation thereof.

10 Claims, 6 Drawing Figures

ANTIBIOTIC COMPOSITIONS CONTAINING VALIDAMYCIN COMPOUNDS

This application is a divisional of Ser. No. 245,135, filed Apr. 18, 1972, now U.S. Pat. 4,011,391.

The present invention relates to validamycins C, D, E and F, and validoxylamines A and B, and acid salts thereof, obtained by cultivating a validamycin-group-producing strain of microorganism belonging to the genus Streptomyces.

In search of new antibiotic substances, the present inventors isolated a large number of soil microorganisms and studied their metabolites. The research work led to the findings that certain soil microorganisms are capable of producing validamycins C, D, E and F, and validoxylamines A and B, that those microorganisms belong to the genus Streptomyces and that it is possible to obtain said antibiotics by cultivating those microorganisms so that the said antibiotics may be accumulated in the culture medium.

This invention is the culmination of the foregoing discoveries. Thus, the invention relates to validamycins C, D, E and F, and validoxylamines A and B, which are prepared by cultivating a validamycin-group producing strain of microorganism belonging to the genus Streptomyces so that the antibiotic may be produced; accumulating the validamycins C, D, E and F, and validoxylamines A and B in the fermented broth; and recovering the antibiotics so accumulated from the fermented broth.

Furthermore, it is found unexpectedly that these validamycins C, D, E and F, and validoxylamines A and B show an excellent controlling effect against plant diseases, for example, the sheath blight of the rice plant by application in vivo, although they show no antimicrobial potency in vitro against bacteria and fungi. Further study has revealed that these validamycins C, D, E and F, and validoxylamines A and B have a peculiar characteristic that only when the plant or soil is treated therewith, they show a strong disease-controlling effect.

Furthermore, the validamycins C, D, E and F, and validoxylamines A and B have been found to be very effective not only against the sheath blight of the rice plant but also against other plant diseases such as the stem rot of rice plant and the damping off and sclerotial blight of vegetables, flowering plants and lumber seedlings. In addition, the validamycins C, D, E and F, and validoxylamines A and B are substantially harmless to men and beasts, as well as to fish, and even when applied in a high concentration, they do not substantially affect the germination, growth, yield and other features of useful plants.

The principal object of this invention is to provide a process for preparing validamycins C, D, E and F, and validoxylamines A and B.

Another object is to provide new validamycins C, D, E and F.

Further object is to provide a fungicide for combating fungal plant diseases showing no substantial phytotoxicity and substantially non-toxic against both human beings and animals as well as fish.

Other objects will be apparent from the description detailed hereinafter in this specification.

Validamycins C, D, E and F, and validoxylamines A and B (hereinafter referred to sometimes as only "the antibiotics") are obtained by cultivation of validamycin-group producing strain belonging to the genus Streptomyces, so long as it is capable of producing these antibiotics. For example, the strain which was isolated from the soil collected in Akashi City, Hyogo Prefecture, Japan by the present inventors and named *Streptomyces hygroscopicus* var. *limoneus* (ATCC No. 21431 and ATCC No. 21432) as well as its related strains, may be employed to particular advantage. These microorganisms are disclosed in co-pending application No. 871,899.

Some of the microbiological and cultural characteristics of above mentioned *Streptomyces hygroscopicus* var *limoneus* are shown below. In the following descriptions of the cultural characteristics, "Rdg," means the color name according to Ridgeway's "Color Standard and Color Nomenclature."

(1) Morphological characteristics

The aerial mycerium of this microorganism is simply branching and spore-bearing hyphae form spiral.

The conidium is ovoid or rectangular, ranging from $1.0-1.3 \mu \times 1.0-1.5 \mu$ and has a smooth surface. This microorganism has no sclerotia, flagellated spores and sporangia.

(2) Cultural characteristics

Unless otherwise specified, the characteristics described below are those observed upon cultivation at 28° C. When the microorganism was grown at temperatures other than 28° C, the particular cultural temperatures are indicated in parentheses.

a. Czapek's agar
    Growth: Colorless, folded.
    Reverse: Raw Sienna (Rdg., III, 17-i) to Sudan Brown (Rdg., III, 15-k).
    Aerial mycelium: Tilleul Buff (Rdg., XL, 17''''-f) to Light Buff (Rdg., XV, 17'-f), partially Mouse Gray (Rdg., LI, 15''''') along the periphery of the colony.
    Soluble pigment: Yellow with a faint brownish tinge.
  b. Glucose Czapek's agar
    Growth: Colorless to Sulphin Yellow (Rdg., IV, 21-i), folded.
    Reverse: Raw Sienna.
    Aerial mycelium: Tilleul Buff to Massicot Yellow (Rdg., XVI, 21'-f), partially Light Olive Gray (Rdg., LI, 23'''''-d) along the periphery of the colony.
    Soluble pigment: Yellow with a faint brownish tinge.
  c. Glycerin Czapek's agar
    Growth: Colorless to Orange Citrine (Rdg., IV, 19-k), folded.
    Reverse: Raw Sienna.
    Aerial mycelium: Tilleul Buff to Massicot Yellow, partially Light Olive Gray.
    Soluble pigment: Yellow with a faint brownish tinge.
  d. Glucose asparagine agar
    Growth: Colorless.
    Reverse: Old Gold (Rdg., XVI, 19'-i) to Antimony Yellow (Rdg., XV, 17'-b) to Cinnamon Brown (Rdg., XV, 15'-k).
    Aerial mycelium: Light Olive Gray to Mouse Gray, with yellow patches and black moist areas.
    Soluble pigment: Light Brown.
  e. Calcium malate agar Growth: Primuline Yellow (Rdg., XVI, 19′)
Reverse: Primuline Yellow.
Aerial mycelium: Scarce at first, but Tilleul Buff to Light Olive Gray later.
Soluble pigment: Pale Yellow.
f. Starch agar
No growth.
g. Modified starch agar with the following components
Soluble starch — 1%
Potassium hydrogen phosphate — 0.3%
Calcium carbonate — 0.3%
Magnesium sulfate — 0.1%
Ammonium sulfate — 0.2%
Sodium chloride — 0.05%
Agar — 2%
Growth: Colorless to Barium Yellow (Rdg., XVI, 23′-d).
Reverse: Deep Colonial Buff (Rdg., XXX, 21″-b) to Snuff Brown (Rdg., XXIX, 15″-k).
Aerial mycelium: Cartridge Buff (Rdg., XXX, 19″-f) to Mouse Gray, with black moist areas.
Soluble pigment: Light Brown Hydrolysis of starch was observed.
h. Tyrosine agar
Growth: Colorless to Strontian Yellow (Rdg., XVI, 23′).
Reverse: Pale Ochraceous Buff (Rdg., XV, 15′-f) to Light Ochraceous Buff (Rdg., XV, 15′-d).
Aerial mycelium: None.
Soluble pigment: None.
i. Yeast extract agar
Growth: Colorless, folded.
Reverse: Cream color (Rdg., XVI, 19′-f).
Aerial mycelium: White.
Soluble pigment: Light Brown.
j. Nutrient agar (37° C)
Growth: Colorless.
Reverse: Colorless.
Aerial mycelium: None.
Soluble pigment: None.
k. Glucose Nutrient agar (37° C)
Growth: Colorless, wrinkled.
Reverse: Cartridge Buff to Pale Ochraceous Buff.
Aerial mycelium: None.
Soluble pigment: None.
l. Nutrient broth (37° C)
Growth: Colorless surface growth, and colorless flocculent growth in the bottom.
Aerial mycelium: None.
Soluble pigment: None.
m. Glucose Nutrient broth (37° C)
Growth: Surface growth, Cartridge Buff, and colorless flocculent growth in the bottom.
Aerial mycelium: None.
Soluble pigment: None.
n. Potato plug
Growth: Colorless to Pale Ochraceous Buff.
Aerial mycelium: Tilleul Buff to Mouse Gray. The plug turns to Sayal Brown (Rdg., XXIX, 15″-i).
o. Carrot plug
Growth: Colorless.
Aerial mycelium: White to Mouse Gray.
The plug turns to Cinnamon Rufous (Rdg., XIV, 11′-i) to Cinnamon Brown.
p. Cellulose
Growth: Chartreuse Yellow (Rdg., XXXI, 25″-d) to Reed Yellow (Rdg., XXX, 23″-b).
Aerial mycelium: Mouse Gray.
Soluble pigment: Pale Yellow.
q. Gelatin (25° C)
Growth: Very poor.
Aerial mycelium: None.
Soluble pigment: None.
Gelatine is liquefied slightly.
The same is true with nutrient gelatin.
r. Whole egg (37° C)
Growth: Colorless.
Aerial mycelium: None.
Soluble pigment: None.
s. Litmus milk (37° C)
Growth: Surface growth, Cream color to Seashell Pink (Rdg., XIV, 11′-f).
Aerial mycelium: None.
The medium is weakly coagulated, then, peptonized to turn to Army Brown (Rdg., XL, 13‴-i) and becomes weakly acidic.
t. Loffler's medium (37° C)
Growth: Naples Yellow (Rdg., XVI, 19′-d) at first and Light Buff later.
Aerial mycelium: None.
Soluble pigment: None.
No liquefaction.
u. Peptone glucose agar
Growth: Charteruse Yellow
Reverse: Honey Yellow (Rdg., XXX 19″).
Aerial mycelium: Thin, Cream Buff (Rdg., XXX 19″-d).
Soluble pigment: Yellow with a brownish tinge.
v. Plain Agar
Growth: Scarce and colorless growth into substance of medium.
Reverse: Colorless to Mouse Gray.
Aerial mycelium: Scarce, Tilleul Buff to Mouse Gray.
Soluble pigment: None.
(3) Physiological properties
 (a) Temperature and pH range.
  No growth at 10° and at 50° C on Bennett's agar or glucose aspargine agar under aerobic conditions.
  Growth occurs at 15°–45° C, and better growth at 37°–45° C. No growth when medium is pH 4. While growth occurs at pH 5–10, the optimum range is pH 6–7.
 (b) Gelatin: Slightly liquefied.
 (c) Starch: Hydrolyzed.
  Dia. of hydrolyzed area/dia. of colony = 33mm/8mm.
 (d) Tyrosinase reaction: Negative.
 (e) Litmus milk: Peptonized. Coagulation, doubtful.
 (f) Reduction of nitrate: Negative.
 (g) Hydrolysis of cellulose: Negative
 (h) Chromogenicity: Negative.
 (i) Product: Validamycin-group antibiotics.
(4) Utilization of carbon sources
Table 1 shows the utilization of carbon sources by the present strain as examined by the method of Pridham et al. (Journal of Bacteriology 56 107-114(1948)).

Table 1

| Utilization of carbon sources by *Streptomyces hygroscopicus* var. *limoneus* | | | |
|---|---|---|---|
| Erythritol | − | Inositol | ++ |
| Adonitol | − | D-mannitol | ++ |

Table 1-continued

Utilization of carbon sources by *Streptomyces hygroscopicus* var.*limoneus*

| | | | |
|---|---|---|---|
| Sorbitol | + | Dulcitol | − |
| D-Xylose | ++ | Trehalose | ++ |
| L-Arabinose | ++ | Salicin | − |
| L-Sorbose | − | Esculin | − |
| D-Galactose | ++ | Inulin | ++ |
| Glucose | ++ | Dextran | + |
| D-Fructose | ++ | Mannose | ++ |
| L-Rhamnose | ++ | Starch | ++ |
| Melibiose | ++ | Glycerol | ++ |
| Maltose | ++ | Sodium acetate | + |
| Sucrose | ++ | Sodium succinate | + |
| Lactose | ++ | Sodium citrate | + |
| Raffinose | ++ | Calcium 2-keto gluconate | − |

++: well utilized; +: fairly utilized;
−: not utilized.

Thus, the present strain shows monopodial branching, the tip of its aerial mycelium being coiled. The conidia have a smooth surface. It gives bright yellow to buff-colored growth on synthetic media, generally; produces no brown soluble pigment on protein-containing media.

The foregoing cultural characteristics were compared with the descriptions given in "Bergey's Manual of Determinative Bacteriology," 7th ed. (The Williams and Wilkins, 1957), S. A. Waksman's "The Actinomycetes," Vol. 2 (The Williams and Wilkins, 1962) and "Ralph Hutter's Systematik der Streptomyceten" (Es. Karugus, 1967), for instance. It was found that the strain resembles *Streptomyces ambofaciens*, *Streptomyces platensis* and *Streptomyces hygroscopicus*.

However, despite of the close resemblance in the color of both vegetative and aerial mycelium, *Streptomyces ambofaciens* and the present strain differ from each other in that the former does not give black moist spots in the aerial mycelium, that it liquefies gelatin in a medium degree and gives yellow flocculent growth in the liquefied part. There also are difference between both organisms in carbon source utilization. *Streptomyces platensis* differentiates itself from the present strain in that the former produces a Deep Olive vegetative mycelium on Czapek's agar, with the reverse of the colony turning dark olive with the passage of time, that it gives cream to dull yellowish growth on starch agar with its aerial mycelium changing in color from white to Mouse Gray with black patches. They are different from each other in carbon source utilization. Comparison of the descriptions of *Streptomyces hygroscopicus* with the cultural characteristics of the present strain shows that the present strain differentiates itself from *Streptomyces hygroscopicus* in that the growth or the reverse of the colony of the present strain shows the light yellow to buff on Czapek's agar (inclusive of glucose Czapek's agar and glycerol Czapek's agar), glucose asparagine agar, calcium malate agar and other media, and produces a yellowish white to yellow aerial mycelium on said Czapek's agar media. However, many of the cultural characteristics of this strain coincide with the stable characteristics of *Streptomyces hygroscopicus* indicated by Tresner and Backus (Applied Microbiology, Vol. 4, p. 243, 1956). Accordingly we identified the present strain as a variety of *Streptomyces hygroscopicus* and designated it as *Streptomyces hygroscopicus* var. *limoneus*.

As a general trait of the genus Streptomyces, their microbiological characteristics are highly mutative and *Streptomyces hygroscopicus* var. *limoneus* is no exception to the rule. For example, its cultural characteristics and pattern of utilization of carbon sources are susceptible to change, and there can be many mutants. Particularly, of this strain, mutants which have yellow aerial mycelia are easily obtained. However, even those mutants may be employed in this invention in so far as they possess the capacity to produce the validamycin-group antibiotics. It does not matter, of course, if the mutants are induced spontaneously or artificially. For purposes of this invention these mutants are the full equivalents of the above-denominated strains.

In the culture medium employed in this invention, assimilable carbon sources, digestible nitrogen sources, inorganic salts and the like are incorporated. If required, there may be added trace elements such as trace nutrients, growth factors, precursors, etc. to the culture medium. The carbon sources which the validamycin-group producing strain assimilates include, among others, hydrocarbon, glucose, sucrose, molasses, starch, dextrin and glycerine. The nitrogen sources include such organic nitrogenous compounds such as meat extract, soybean flour, corn steep liquor, peptone, casein, etc., as well as such inorganic nitrogen compounds as nitrates and ammonium compounds, and any of them can be employed to advantage.

While cultivation can be carried out by surface culture, it is more usual to adopt the aerobic submerged culture. In the case of the submerged culture, the pH of the medium is preferably near neutral, and while growth occurs at the incubation temperature of 20° to 40° C, it is preferable to maintain the medium within the range of about 23° to 37° C. The accumulation of the objective antibiotic completes in 4 to 7 days.

The antibiotics do not inhibit the growth of bacteria and fungi in vitro but only cause *Pellicularia sasakii* and its closely related fungi an abnormal branching (excessive branching, or branched hyphae become an umbel like form) on the tips of the hyphae. Therefore, the bioassay of the antibiotics should be conducted in the following manner.

*Pellicularia sasakii* is used as the test organism employing plain agar as the assay medium. The test organism is cultivated on a potato (sucrose) agar slant for 2 to 5 days, and the resulting culture is used to inoculate at the center of a 9-cm Petri dish plate of modified Pfeffer's medium, which is then incubated at 27° C for 2 days. By the end of this period, the mycelium will have spread over the entire surface of the plate. The growth on the circumference about 3 to 3.5 cm in radius from the center is cut out with a cork borer and the agar disc thus obtained is used as the inoculum.

A serial dilution series of agar plants containing varying concentrations of the antibiotics is prepared in the same manner as a conventional agar dilution method.

A glass disc of 8 mm in diameter and about 0.2 mm thick, is placed in the center of each of the aforementioned dilution series of agar plates, and the agar disc inoculum is then placed on the glass disc. After incubation at 27° C for 40 hours, the result is evaluated. Naked-eye examination reveals that, in *Pellicularia sasakii*, the tip of hyphae of test organism growing from the agar disc inoculum undergoes abnormal branching. The term dilution unit means the value of maximum dilution which produces such abnormal branching. The aqueous solution containing 1000 γ/ml. of purified validamycins C, D, E and F, and validoxylamines A and B shows 100, 10, 80000, 80000, 100 and 10 dilution unit/ml., respectively.

Modified Pfeffer's medium, which is employed in this assay, has the following composition.

| | |
|---|---|
| Sucrose | 3% |
| L-asparagine | 0.2% |
| Ammonium nitrate | 0.3% |
| Potassium dihydrogen phosphate | 0.1% |
| Magnesium sulfate | 0.1% |
| Velsenol* (Dow Chemical) | 0.001% |
| Agar   Adjusted to pH 7. | 1.2% |

*A chelate compound, iron sodium ethanol ethylene diamine triacetate

Before using the medium, the following vitamins are added in the specified amounts. (Weight per ml. of medium)

| | |
|---|---|
| Thiamine | 1 γ/ml. |
| Riboflavin | 1 γ/ml. |
| Calcium pantothenate | 1 γ/ml. |
| Niacin | 1 γ/ml. |
| Riotin | 0.005 γ/ml. |
| Folic acid | 0.5 γ/ml. |
| Pyridoxine hydrochloride | 2 γ/ml. |
| p-Aminobenzoic acid | 0.5 γ/ml. |
| Cyanocobalamine | 0.0002 γ/ml. |

When *Streptomyces hygroscopicus* var. *limoneus* is cultivated in the above manner, the antibiotics are produced and accumulated mainly in the liquid phase of the broth. Therefore, to recover these antibiotics, it is preferable to filter the broth and then recover the antibiotics from the resulting filtrate. When the microorganism employed is capable of producing only one of the antibiotics, the antibiotics can, of course, be collected from the culture broth in per se conventional manner. But, in case where the microorganism employed can produce simultaneously two or more of them, they are concomitantly accumulated in the broth, so that those antibiotics are collected from the broth, as a mixture of them or as an individual validamycins C, D, E or F, or validoxylamines A or B.

For the purpose of isolating the antibiotics, means which are conventionally used to recover the metabolites of microorganisms from their broths can be employed either singly or in combination. Thus, the means include such techniques as filtration, concentration, ion-exchange chromatography with ion exchangers, adsorption chromatography on active carbon, silica gel or alumina, gel filtration with Sephadex (Trade name of Pharmacia) or Bio-Gel-P (Trade name of BIO. RAD Laboratories), the use of various solvents to bring the solute into another liquid phase, precipitation, removal of impurities, dialysis, drying and recrystallization, among others.

For the separation and purification of the antibiotics from impurities, for example, its water soluble and basic properties are used, e.g., while water soluble lower molecular impurities are not adsorbed, the antibiotics can be adsorbed on active carbon and eluted with an acidified aqueous alcohol and/or aqueous acetone.

The antibiotics can be adsorbed strongly on cation exchange resins even when they are in a state of neutral or weakly acid solution, and eluted with a buffered basic solution, or an aqueous salt solution.

The aforementioned salts not only include the alkali salts of strong acids such as sodium chloride and ammonium chloride but also the alkali salts of organic acids such as sodium acetate, and ammonium acetate, as well as the salts of weak acids or weak bases such as those of acetic acid, and pyridine.

The antibiotics can be adsorbed weakly also on strong anion exchange resins and eluted with water.

Among the ion exchange resins (strong or weak) which can be employed for the aforesaid purpose, there may be mentioned, for example, Amberlite IR-100, 112 & 120, Amberlite XE-69, Amberlite IRC-50, Amberlite XE-89, Amberlite XE-64, Amberlite IR-45 & IRA-900 (All the above resins are the Trade Name of Rohm and Haas, Co.), Dowex-50W×2, Dowex-1×2, Dowex-1×8 (These three resins are the Trade Name of Dow Chemical, Co.), Duolite CS-65 (Trade Name of Chemical Process, Co.), Permutit-50 (Trade Name is Permutit, Co.), etc. These resins may be prepared by such methods as described in "Ion Exchange Resin" (Robert Kumin, Published by John Wiley & Sons, Inc., New York, N.Y., U.S.A. PP.).

The separation of the antibiotics are carried out by ion exchange chromatography using cation and anion exchange resins. For example, in a typical column chromatography for preparative purposes, the crude validamycins are chromatographed on Dowex 1×2 column (OH form, 100 - 200 mesh, 870 ml.), and the column is developed with water to give the six components: Validoxylamines A and B and validamycins D, C, F and E, in order of elution from the column. Validamycin C-rich fractions and a fraction mainly containing validamycin D are rechromatographed on a silica gel column (elution with n-propanol, acetic acid, water 4:1:1) and Dowex 50W×2 column (elution with pyridine-acetic acid buffer, pH 6.0). Validamycins E and F are retarded on Dowex 1×2 column owing to their great affinity for the resin, these show a rather diffuse elution pattern on a gravity flow. The complete separation of validamycins E and F is not accomplished on Dowex 1×2 column. Validamycin E-rich fractions are validamycin F-rich fractions obtained by Dowex 1×2 chromatography are further chromatographed on Dowex 50W×2 column (elution with pyridine-acetic acid buffer, pH 6.0). In this chromatography, early fractions contain validamycin F. Thereafter, validamycin E is eluted.

Finally, chromatographically homogeneous validamycins C, D, E and F are obtained by rechromatography on Dowex 1×2 (OH form, developed with water). Validoxylamine A is eluted just before validamycin D on Dowex 1×2 column, and crystallization from water-ethanol give a pure validoxylamine A. Although validoxylamine B and validamycin D are almost overlapped on Dowex 1×2 chromatography, these components are easily separated on Dowex 50W×2 column (elution with pyridine-acetic acid buffer, pH 6.0).

By using the foregoing procedures, validamycins C, D, E and F, and validoxylamines A and B are successfully isolated from a culture broth of *Streptomyces hygroscopicus* var. *limoneus*.

Each of validamycins C, D, E and F is obtained as a white powder and gives rise to validoxylamine A and D-glucose upon hydrolysis. However, those antibiotics are differ from one another in molecular structure, i.e. in the configuration of glycosidic bonds in the D-glucose moieties (α-or β-configuration) and in the positions and in the number of D-glucose molecules.

The physicochemical properties of the validamycins C, D, E and F, and validoxylamines A and B are set forth below.

1. Structural formula (a) Validamycin C

[R: O-α-D-glucopyranosyl-3-hydroxymethyl-4,5,6-trihydroxy-2-cyclohexenyl group.]

(b) Validamycin D

[R₁: O-α-D-glucopyranosyl-2,3,4-trihydroxy-5-hydroxymethylcyclohexyl group.]

(c) Validamycin E

[R₂: O-α-D-glucopyranosyl-O-β-D-glucopyranosyl group.]

(d) Validamycin F

[R₃: O-α-D-glucopyranosyl-3-hydroxymethyl-4,5,6-trihydroxy-2-cyclohexenyl group.]

(e) Validoxylamine A (f) Validoxylamine B

[R₀: 2,3,4,6-tetrahydroxy-5-hydroxymethyl-cyclohexyl group.]

2. Melting or decomposition points

While none of validamycins C, D and E, and validoxylamines A and B has a definite melting point, they are gradually decomposed at the following temperatures.

| | |
|---|---|
| Validamycin C: | 142° – 160° C |
| Validamycin D: | 125° – 130° C |
| Validamycin E: | 263° – 268° C |
| Validamycin F: | 165° – 173° C |
| Validoxylamine A: | 101° – 105° C |
| Validoxylamine B: | 102° – 108° C |

3. The elementary analysis, the molecular formulas as calculated therefrom, pKa' values, neutralization equivalents (molecular weight) and optical rotation values are given in Table 2.

methylsulfoxide, except that validoxylamine B is more sparingly soluble in pyridine.

In methanol, validamycin D and validoxylamine A are soluble but validamycins C, E and F, and validoxylamine B are more sparingly soluble.

Table 2
A table of the physicochemical properties of validamycins C to F and validoxylamines A and B

| Data Compound | Estimated molecular formula | Molecular weight | Elementary analysis % Found | Elementary analysis % Calculated | Optical rotation $[\alpha]D(H_2O)$ | pKa' (neutralization equivalent, in aqueous solution) | TLC Rf ** (silica gel G) | The number of D-glucose units and their bond mode*** |
|---|---|---|---|---|---|---|---|---|
| Validoxyl-amine A | $C_{14}H_{25}NO_8$ $H_2O$ | 353.4 (335.4)* | C 47.86 H 7.86 N 3.89 | C 47.58 H 7.70 N 3.96 | +170.0° | 6.2 ± 0.2 (355 ± 30) | 0.34 | — |
| B | $C_{14}H_{25}NO_9$ $H_2O$ | 369.4 (351.4)* | C 46.01 H 7.28 N 3.59 | C 45.52 H 7.36 N 3.79 | +172.4° | 5.0 ± 0.2 (370 ± 30) | 0.42 | — |
| Valida-mycin C | $C_{26}H_{45}NO_{18}$ $H_2O$ | 677.7 * (659.7) | C 46.48 H 7.22 N 2.15 | C 46.08 H 6.99 N 2.07 | | 6.0 ± 0.2 (680 ± 30) | 0.15 α-and | 2 β-bonds |
| D | $C_{20}H_{35}NO_{13}$ $H_2O$ | 515.5 * (497.5) | C 46.97 H 7.23 N 2.58 | C 46.60 H 7.24 N 2.72 | +169.3° | 6.0 ± 0.2 (520 ± 30) | 0.24 | 1 α-bond |
| E | $C_{26}H_{45}NO_{18}$ $H_2O$ | 677.7 * (659.7) | C 46.22 H 7.19 N 1.94 | C 46.08 H 7.02 N 2.07 | +148.2° | 6.1 ± 0.2 (660 ± 30) | 0.15 | 2 α-and β-bonds |
| F | $C_{26}H_{45}NO_{18}$ $H_2O$ | 677.7 * (659.7) | C 46.00 H 6.90 N 1.95 | C 46.08 H 7.02 N 2.07 | +130.7° | 6.1 ± 0.2 (680 ± 30) | 0.15 | 2 α-and β-bonds |
| Validoxyl-amine A | $C_{14}H_{25}NO_8$ $H_2O$ | 353.4 (335.4)* | C 47.86 H 7.86 N 3.89 | C 47.58 H 7.70 N 3.96 | +170.0° | 6.2 ± 0.2 (355 ± 30) | 0.34 | — |
| B | $C_{14}H_{25}NO_9$ $H_2O$ | 369.4 (351.4)* | C 46.01 H 7.28 N 3.59 | C 45.52 H 7.36 N 3.79 | +172.4° | 5.0 ± 0.2 (370 ± 30) | 0.42 | — |
| Valida-mycin C | $C_{26}H_{45}NO_{18}$ $H_2O$ | 677.7 * (659.7) | C 46.48 H 7.22 N 2.15 | C 46.08 H 6.99 N 2.07 | | 6.0 ± 0.2 (680 ± 30) | 0.15 | 2 α-and β-bonds |
| D | $C_{20}H_{35}NO_{13}$ $H_2O$ | 515.5 * (497.5) | C 46.97 H 7.23 N 2.58 | C 46.60 H 7.24 N 2.72 | +169.3° | 6.0 ± 0.2 (520 ± 30) | 0.24 | 1 α-and |
| E | $C_{26}H_{45}NO_{18}$ $H_2O$ | 677.7 * (659.7) | C 46.22 H 7.19 N 1.94 | C 46.08 H 7.02 N 2.07 | +148.2° | 6.1 ± 0.2 (660 ± 30) | 0.15 α-and | 2 β-bonds |
| F | $C_{26}H_{45}NO_{18}$ $H_2O$ | 677.7 * (659.7) | C 46.00 H 6.90 N 1.95 | C 46.08 H 7.02 N 2.07 | +130.7° | 6.1 ± 0.2 (680 ± 30) | 0.15 | 2 α-and β-bonds |

*The figure in parentheses denotes the empirical molecular weight as calculated to the exclusion of $H_2O$.
**Developer solvent: n-propanol-acetic acid-water: 4/1/1.
***Estimated from the spin-spin coupling constant and optical rotation value.

4. Ultraviolet absorption spectrum

When measured in an aqueous solution, validamycins C, D, E and F and validoxylamines A and B show no characteristic absorption maxima on the ultraviolet region of the spectrum above 210 mμ excepting terminal absorptions.

Figure 1:
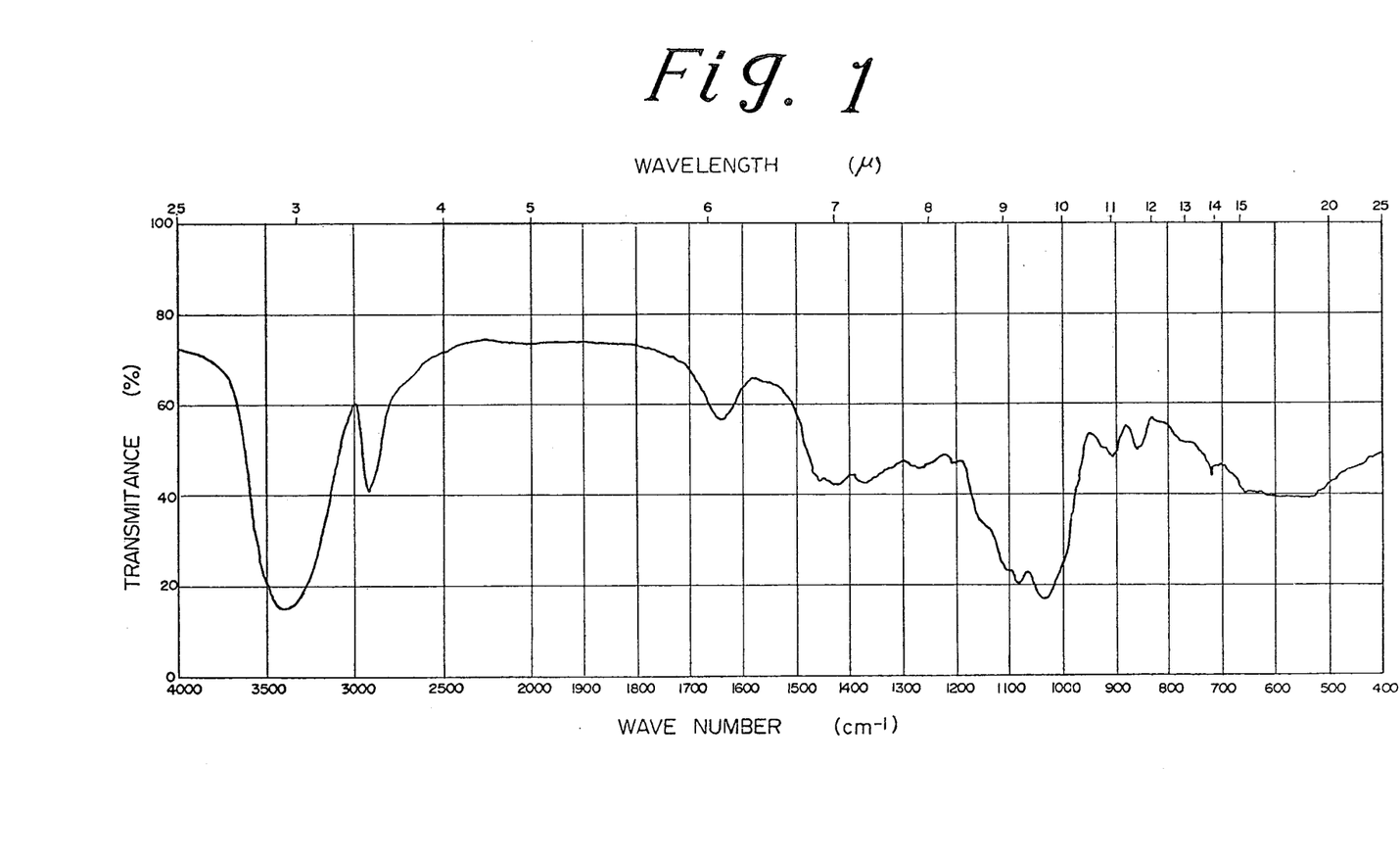
Figure 2:
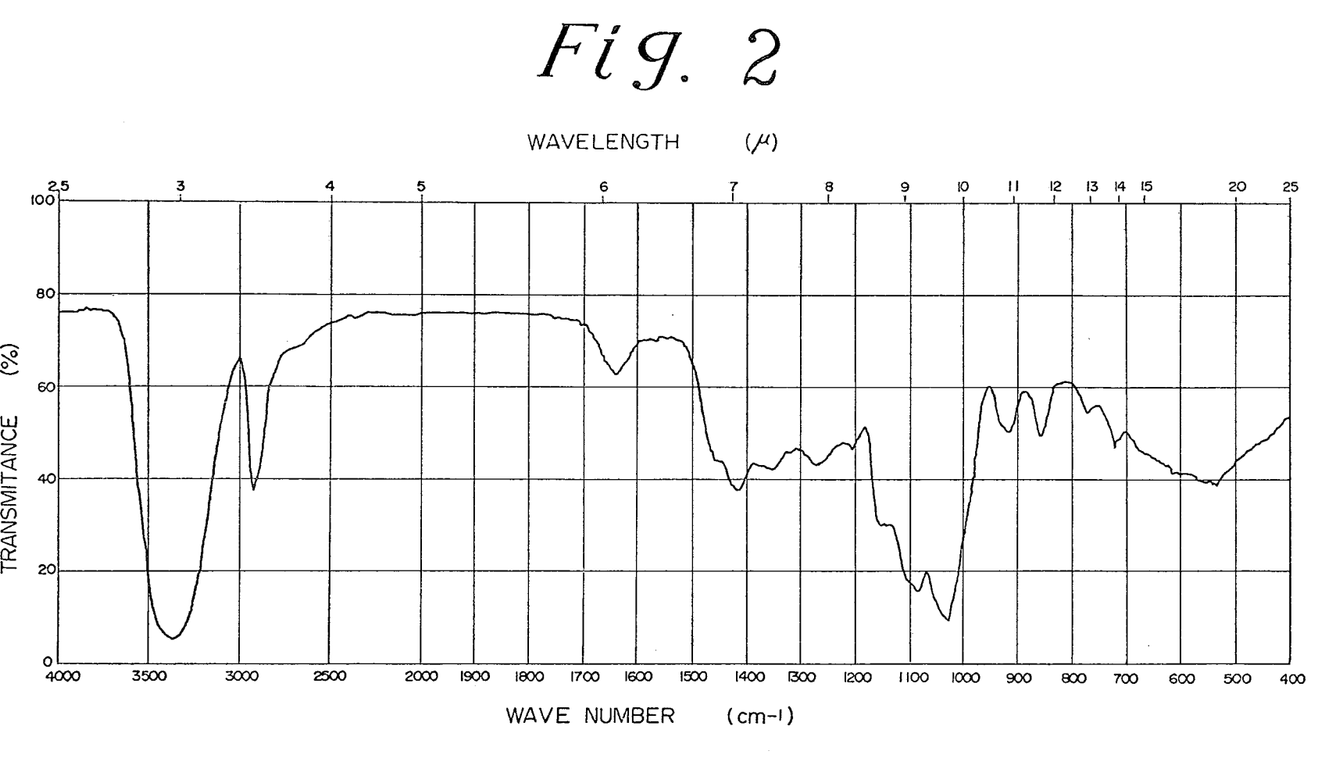
Figure 3:
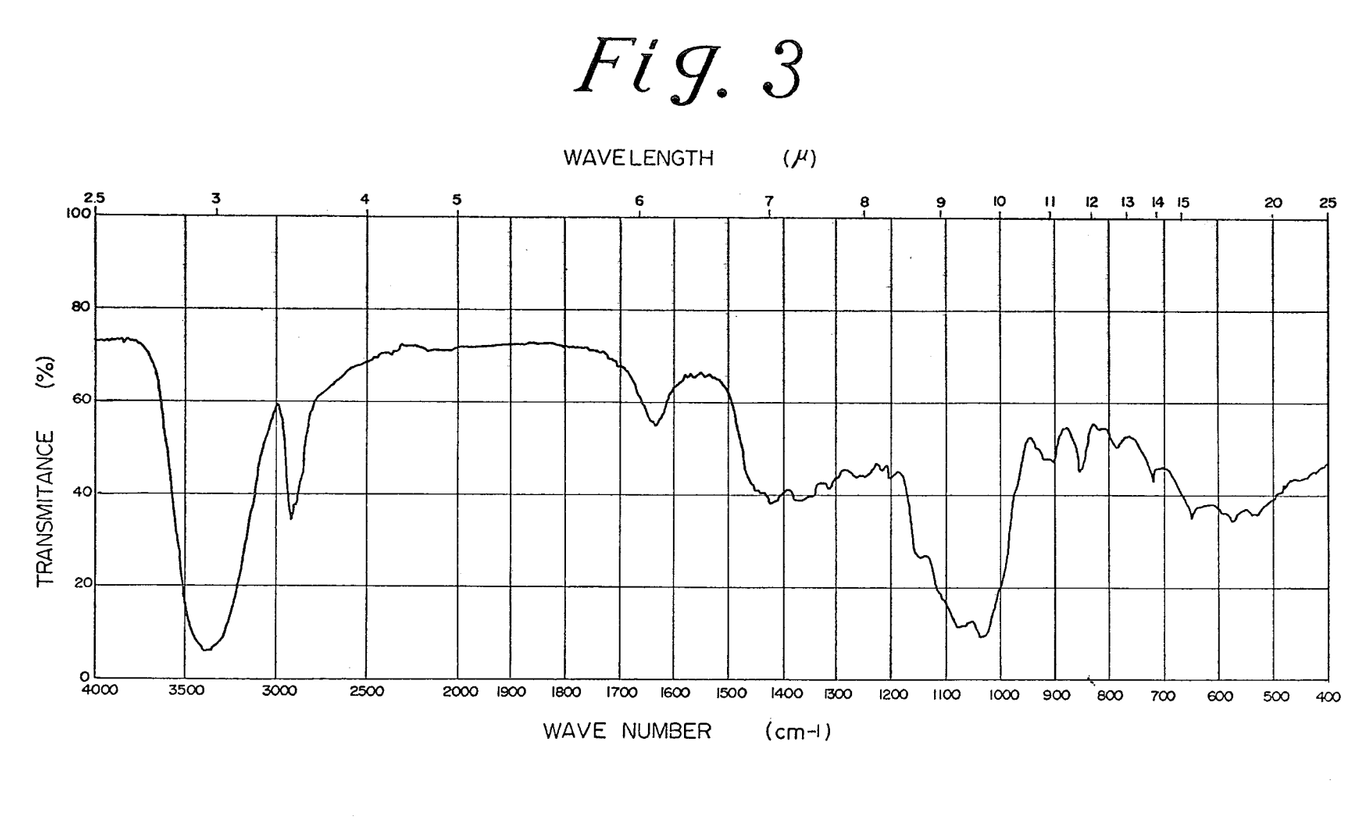
Figure 4:
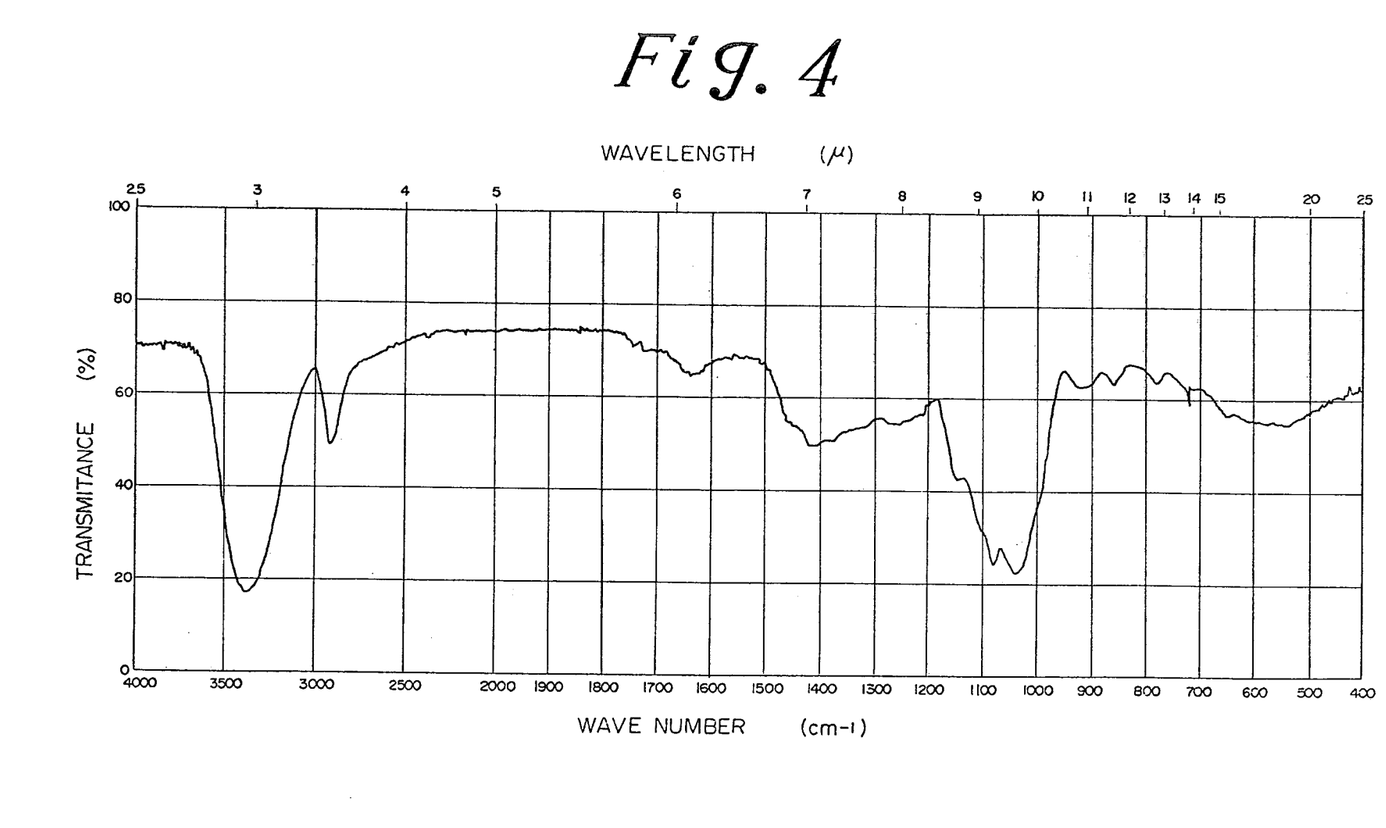
Figure 5:
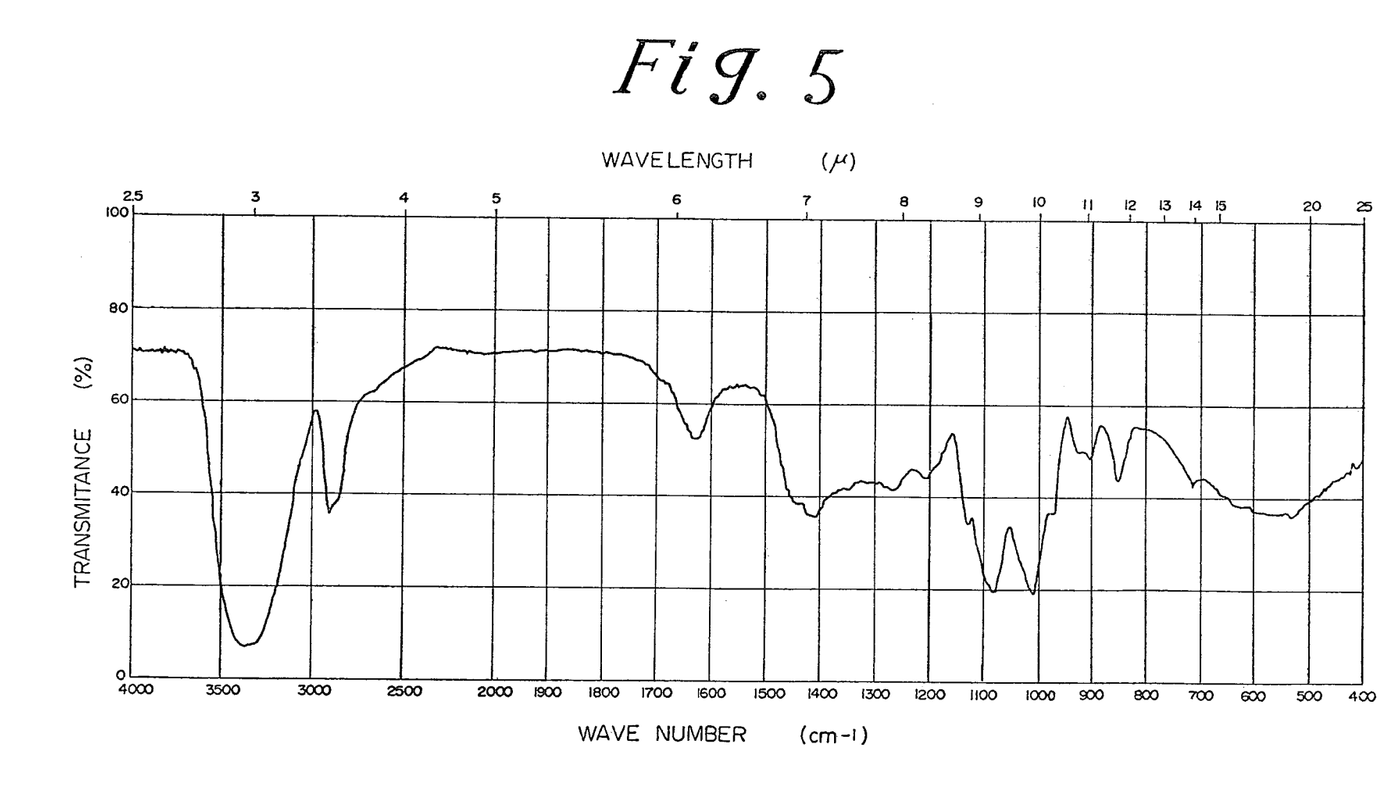
Figure 6:
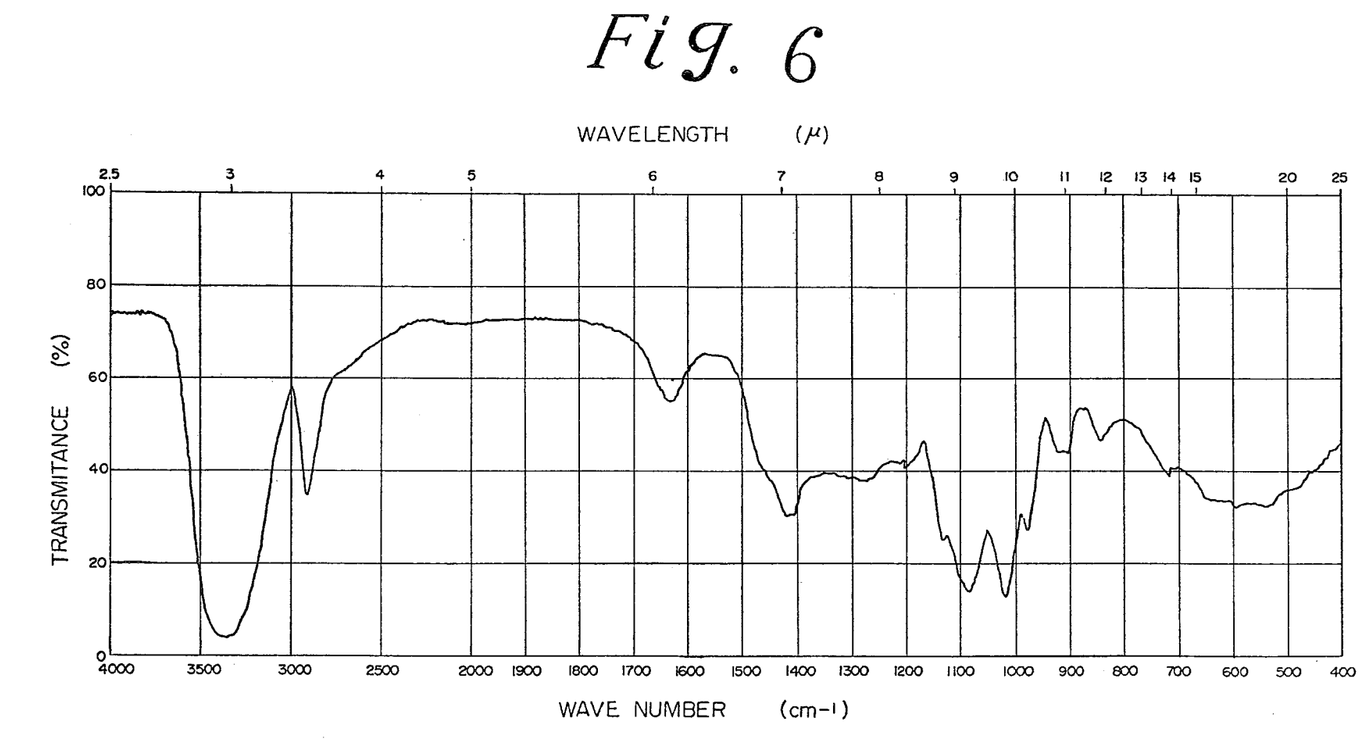

5. Infrared absorption spectrum (FIGS. 1 to 6)

The absorption spectra of validamycins C, D, E and F and validoxylamines A and B as measured by the potassium bromide disc method are reproduced in FIGS. 1 to 6, respectively. It will be seen that their absorption spectra are closely similar to one another. The dominant absorptions of validamycins C, D, E and F, and validoxylamines A and B are as follows.

3400 (S), 2910 (M), 1638 (M), 1410 (M), 1075 (S), 1025 (S), 900 (M), 845 (M)

The abbreviations "M," "W" and "S" in parentheses denote medium absorptions, weak absorptions and strong absorptions.

6. Solubilities

Each of the antibiotics is readily soluble in water and soluble in pyridine, dimethylformamide and di- 7. Color reactions Each of the antibiotics gives positive reactions in periodic acid-benzidine and Greig-Leaback reagent (t-butylhypochlorite reagent) tests but gives negative reactions in Sakaguchi and Elson-Morgan tests.

Validamycins C, D, E and F, and validoxylamines A and B also give positive reactions in anthrone, orcinsulfuric acid and naphthoresorcinol-sulfuric acid tests.

8. Acid salt

The validamycins C, D, E and F have the weak base-property, forms a salt with acid (e.g. hydrochloric acid, sulfuric acid, etc.). For example, the melting or decomposition points, elementary analysis of the hydrochloride of validamycins C, D, E and F are as following Table 3.

Table 3

| Compound | Decomposition points | Elementary analysis | |
|---|---|---|---|
| Validamycin C.HCl | 115° – 132° C | C, 44.56 N, 1.53 | H, 6.32 Cl, 5.24 |
| Validamycin D.HCl | 113° – 128° C | C, 44.61 N, 2.72 | H, 6.96 Cl, 6.74 |
| Validamycin E.HCl | 141° –157° C | C, 44.72 N, 1.72 | H, 6.54 Cl, 5.41 |
| Validamycin F.HCl | 146° – 164° C | C, 44.83 N, 1.95 | H, 6.59 Cl, 5.32 |

9. Ester

The hydroxyl groups of validamycins C, D, E and F can be esterified with an acid (e.g. acetic acid, malonic acid or malic acid). For example, the melting point or decomposition points, elementary analysis of the acetate of validamycins C, D, E and F are as following Table 4.

Table 4

| Compound | Decomposition point | Elementary analysis | |
|---|---|---|---|
| Acetyl validamycin C | 98° –105° C | C, 51.45 N, 1.04 | H, 5.73 |
| Acetyl validamycin D | 94° – 106° C | C, 52.86 N, 1.44 | H, 6.23 |
| Acetyl validamycin E | 96° – 107° C | C, 51.57 N, 1.21 | H, 5.80 |
| Acetyl validamycin F | 103° – 108° C | C, 51.48 N, 1.26 | H, 5.89 |

10. Acute toxicity of the antibiotics

The toxicity of the antibiotics can be confirmed, for instance, by administering each of the validamycins C, D, E and F, and validoxylamines A and B, intravenously to mice and measuring the $LD_{50}$ value, or by measuring the median lethal dose (48 hours) for *Oryzias latipes*. The results of such measurements are shown in Table 5.

Table 5

| Test animal | Antibiotics | Acute toxicity | |
|---|---|---|---|
| | | Test procedure | Toxicity |
| Mice | Validamycin C | Intravenous injection | $LD_{50}$ > 2000 mg/kg |
| | Validamycin D | | $LD_{50}$ > 2000 mg/kg |
| | Validamycin E | | $LD_{50}$ > 2000 mg/kg |
| | Validamycin F | | $LD_{50}$ > 2000 mg/kg |
| | Validoxylamine A | | $LD_{50}$ > 2000 mg/kg |
| | Validoxylamine B | | $LD_{50}$ > 2000 mg/kg |
| Oryzias latipes | Validamycin C | Leaving in water solution | $TL_m$ > 1000 ppm |
| | Validamycin D | | $TL_m$ > 1000 ppm |
| | Validamycin E | | $TL_m$ > 1000 ppm |
| | Validamycin F | | $TL_m$ > 1000 ppm |
| | Validoxylamine A | | $TL_m$ > 1000 ppm |
| | Validoxylamine B | | $TL_m$ > 1000 ppm |

The biological properties

When a 1 mg./ml. aqueous solution of each of validamycins C, D, E and F and validoxylamines A and B is used as a stock solution, the highest dilution factor that causes an abnormal branching at the hyphal tips of *Pellicularia sasakii* is as follows.

| | |
|---|---|
| Validoxylamin A | 100 |
| Validoxylamine B | 10 |
| Validamycin C | 100 |
| Validamycin D | 10 |
| Validamycin E | 70,000 – 80,000 |
| Validamycin F | 70,000 – 80,000 |

Thus obtained validamycins C, D, E and F and validoxylamines A and B can be employed for combating the plant diseases. For the purpose, they are used in the form containing the cultured broth of a validamycin-group producing strain belonging to the genus Streptomyces, filtrate thereof, the concentrate thereof, or a purified preparation thereof. It is also possible to employ validamycins C, D, E and F and validoxylamines A and B in the form of a free base or as the salts with suitable organic or inorganic acid (i.e. oxalic acid, succinic acid, sulfuric acid, hydrochloric acid, etc.) or as complexes with metals (e.g. sodium, cobalt, copper, aluminum, calcium, etc.). It is further permissible to employ an ester of the antibiotics, for instance, which may be obtained by esterifying the hydroxyl of the antibiotics with an acid (e.g. acetic acid, malonic acid or malic acid).

These composition can be applied in any suitable manner. Thus, depending upon the purpose of application, application time, application method, etc., the composition may be directly applied as such, after dissolution or dispersion in a suitable liquid carrier, or after blending with a suitable solid carrier. If desired, by adding an emulsifying agent, dispersant, suspending agent, adsorbent, penetrant, wetting agent, thickener, stabilizer or/and adjuvant, the present composition may be used in such varied formulations as an oil solution, emulsion, wettable powder, aqeuous solution, soluble powder, dust, tablet, granule and spray, etc.

It is further allowable to use such a composition after compounding or blending with such other germicides as copper germicides, organic sulfur germicides, organic chlorine germicides, organic phosphorus germicides, other antibiotics, etc., such insecticides as organic chlorine insecticides, organic phosphorus insecticides, carbamic acid insecticides, natural insecticides, etc., ascaricides, nematocides, herbicides, plant growth regulators, synergistic agents, attractants, repellents, perfumes, plant nutrients, fertilizers and the like.

A concentration of the active ingredient in the present fungicides ready for use is usually from about 0.0001% to about 0.5% by weight, more preferably about 0.0003% to about 0.3% by weight, in case of the liquid form (i.e. a solution, a suspension or an emulsion); while in case of the solid composition, from about 0.01% to about 30% by weight, about 0.1% to about 20% by weight is preferable. But, upon necessity, a composition containing at a higher or lower concentration than the above-mentioned value may be put into use. The content of the active ingredient of composition may be in from about 0.5% to about 80% by weight in relative to the composition, when it is prepared for a concentrate form.

Some formulations of the fungicide containing validamycins C, D, E and F and validoxylamines A and B are illustrated as follows:

| Formulation 1 | |
|---|---|
| Wettable powder | |
| Validamycin C | 1.0% |
| Sodium ligninsulfonate | 0.1% |
| Polyoxyethylene nonylphenyl ether | 0.1% |
| White carbon | 0.1% |
| Clay | 98.7% |

Depending upon the purpose and method of application, the above formulation is diluted with water to the range of 2 – 400 ppm in terms of the present antibiotic and the diluted preparation is sprayed by means of a sprayer, applied to the soil surface, or the above powder is used undilutedly to coat the seed.

| Formulation 2 | |
|---|---|
| Tablets | |
| Validamycin E | 15.0% |
| Polyoxyethylene nonylphenyl ether | 2.0% |
| Lactose | 83.0% |

Before application, the above formulation is dissolved in water to make the concentration range shown in Formulation 1.

| Formulation 3 | |
|---|---|
| Aqueous solution | |
| Validamycin D | 40.0% |
| Methanol | 5.0% |
| Aluminum stearate | 5.0% |
| Water | 50.0% |

The above formulation is diluted with water to the range of 1,000 – 200,000 ppm. and the diluted preparation is sprayed by means of a fine concentrate sprayer from aircraft, for instance.

| Formulation 4 | |
|---|---|
| Emulsifiable concentrate | |
| Validamycin F | 10.0% |
| Polyoxyethylene nonylphenyl ether | 5.0% |
| Methanol | 20.0% |
| Methylnaphthalene | 40.0% |
| Dimethylformamide | 25.0% |

Before application, the above formulation is diluted with water to the concentration range given in Formulation 1.

| Formulation 5 | |
|---|---|
| Dust | |
| Validoxylamine A | 3.0% |
| Aluminum stearate | 0.02% |
| Talc | 96.98% |

Depending upon the objective and mode of application, the above mixture as such is dusted by means of a duster at the rate of 1 – 6 kg. to 10 are, or used to coat the seed.

| Formulation 6 | |
|---|---|
| Mixed dust A | |
| Validamycin E | 4.0% |
| Validamycin F | 1.0% |
| Aluminum stearate | 0.02% |
| Talc | 94.98% |

The above preparation is directly applied at the rate of 1 – 50% per seeds weight to coat the seed.

EXPERIMENT 1

Rice sheath blight control test (Test procedure)

Test plants:

Rice Plants (variety: *kinmaze*) are planted in earthen pots 9 cm in diameter, 3 stocks per pot. Seedlings 80 days after potting are tested and 6 pots each of them are grouped.

Inoculating method:

Pathogenic fungi *Pellicularia sasakii* is cultivated on a plate of potato infusion-sugar-agar at 30°C for 48 hours, and its agar disc 10mm in diameter is cut out from a peripheral colony. The disc is inserted into the inside space of the leaf sheath near the soil surface, a disc per stem. The pots are kept in a PVC shelter at the temperature of 32°–25° C and the relative humidity of 100–70%. Inoculation is carried out immediately after the applied drug has been air-dried in the prophylactic test, and 3 days before application in the remedial test.

Application of the drug

Each of test drugs is diluted in water to prepare the fixed concentration of the active ingredient, as shown in Table 3, and the aqueous solution is sprayed evenly over the foliage by means of a spray-gun at the rate of 30 ml. per 6 pots.

Assay method:

10 days after application of the drug, the length of each stem from ground level to the upper edge of the lesion is directly measured.

Table 6

| | | Leaf blight control effect | | | | | | | | | | |
|---|---|---|---|---|---|---|---|---|---|---|---|---|
| | | (The average length of lesions/stem(cm)) | | | | | | | | | | |
| | Concentration | Preventive effect[a] (%) | | | | | Remedial effect[a] (%) | | | | | Injury to plant |
| drug | of drug (ppm) | 3 | 10 | 30 | 100 | 300 | 1 | 3 | 10 | 30 | 100 | 300 | (300ppm) |
| Validamycin C | | 46 | 34 | 4 | 1 | 0 | — | 68 | 22 | 12 | 10 | 7 | — |
| Validamycin D | | 28 | 5 | 1 | 0 | 0 | — | — | 99 | 20 | 11 | 8 | — |
| Validamycin E | | 3 | 2 | 0 | 0 | 0 | 41 | 14 | 12 | 11 | 5 | 3 | — |
| Validamycin F | | 21 | 2 | 0 | 0 | 0 | 27 | 13 | 13 | 12 | 12 | 2 | — |
| Validamycin E + F[b] | | 1 | 0 | 0 | 0 | 0 | 9 | 5 | 3 | 2 | 1 | 1 | — |
| Validoxylamine A | | 28 | 4 | 1 | 0 | 0 | — | 83 | 28 | 14 | 10 | 7 | — |
| Validoxylamine B | | 49 | 47 | 32 | 16 | 8 | — | — | 93 | 75 | 51 | 10 | — |
| MAFA[c] | | 76 | 51 | 0 | 0 | 0 | — | 89 | 30 | 15 | 13 | 10 | + |

[a]Percent of the average length of lesion/stem(cm) per control untreated (34.4cm)
[b]Mixture of validamycins E (80%) and F (20%)
[c]Methyl arsonic acid ammonium complex salt Experiment 2

Cucumber damping-off control test (Test procedure)

*Rhyzoctonia solani* is cultured on barley medium at 28° C for 5 days. A field soil sample is packed into clay pots 9 cm in diameter, which are then sterilized with steam. The chaff inoculum is evenly worked into the cover soil of each pot to the depth of about 3 cm, at the rate of 2g./pot. The pots are kept in an incubation chamber at 28° C for 4 days and, then, transferred to a greenhouse.

Application of the drug:

As per Experiment 1, the drug is sprayed onto the soil surface at the rate of 30 ml./6 pots/group.

Test plant:

Healthy seeds of cucumber (variety: Yonyo) are sown by burial in the pots immediately after treatment, at the rate of 10 seeds/pot. The pots are then placed in a greenhouse at 32°–28° C.

Assay method:

14 days after sowing, the results are evaluated against the following coefficients of lesion and the degrees of damage are calculated.

Coefficients of lesion (I)

0 : Healthy
0.5 : Root hairs alone are slightly affected.
1 : Aerial portions near soil surface and roots affected.
2 : Early stage of damping-off.
3 : Affected at germination; growth inhibited.

Degree of damage (%) = $(\Sigma(nI))/3 \times N \times 100$ wherein $n$ means the number of samples corresponding to each coefficient of lesion and N means the total number of plants.

Table 7

| Drug | Concentration of drug (ppm) | Degree of damage (%) | Injury to plant |
|---|---|---|---|
| Untreated control | — | 100 | — |
| Validamycin C | 5 | 100 | — |
|  | 20 | 84 | — |
|  | 80 | 0 | — |
| Validamycin D | 5 | 100 | — |
|  | 20 | 93 | — |
|  | 80 | 0 | — |
| Validamycin E | 5 | 10 | — |
|  | 20 | 0 | — |
|  | 80 | 0 | — |
| Validamycin F | 5 | 80 | — |
|  | 20 | 0 | — |
|  | 80 | 0 | — |
| Validamycin(E + F) | 5(4 + 1) | 7 | — |
|  | 20(16 + 4) | 0 | — |
|  | 80(64 + 16) | 0 | — |
| Validoxylamine A | 5 | 84 | — |
|  | 20 | 6 | — |
|  | 80 | 0 | — |
| Validoxylamine B | 5 | 100 | — |
|  | 20 | 100 | — |
|  | 80 | 75 | — |
| Pentachloro-nitrobenzene | 5 | 100 | — |
|  | 20 | 100 | — |
|  | 80 | 100 | — |

Experiment 3

Tomato leaf mold control test (Test procedure)

Test plants:

Tomato plants (variety: *ponterosa*) are planted in 12 cm in diameter pots, one plant per pot. The seedlings 50 days after potting are used, 6 pots/group.

Application of the drug:

Applied at the rate of 100 ml./6 pots/group as per Experiment 1.

Inoculating method:

Pathogenic fungi *Cladosporium fulvum* in cultured on a potato infusion-sucrose plate at 20° C for 14 days, and a suspension of conidia ($5 \times 10^5$/ml.) is prepared from the culture.

The plants are spray-inoculated with the suspension 3 days before application of the drug, at the rate of 5 ml. per pot. The pots are kept in an inoculation chamber at 25° C for 24 hours, and, then they are transferred to a greenhouse.

Assay method:

14 days after inoculation, the specific ratio of the average area of lesion in the leaves is measured.

Table 8

| Drug | Concentration of drug of lesion (ppm) | Specific area Injury to (%) | plant |
|---|---|---|---|
| Untreated control | — | 98 | — |
| Validamycin C | 50 | 18 | — |
| Validamycin D | 50 | 18 | — |
| Validamycin D | 50 | 25 | — |
| Validamycin E | 50 | 2 | — |
| Validamycin F | 50 | 3 | — |
| Validamycin (E+F)[a] |  |  |  |
| Validoxylamine A | 50 | 6 | — |
| Validoxylamine B | 50 | 36 | — |

[a]Mixture of validamycins E (80%) and F (20%).

The followings are examples for production of the antibiotics and the liquid-chromatographic equipment to be used for analysis in these examples are as follows. For separation and feeding, the JLC-BC$_2$ equipment manufactured by Japan Electronics Co., Ltd. is employed.

For the detection of active compounds giving a negative orcin-sulfuric acid test, the differential refractometer model R 403 (Water Associates, Inc.) is utilized.

The following conditions were employed.

(Analysis I)

Analytical column:

A column (70 cm × 8 mm I.D.) packed with the resin AG 1 × 2 (200-400 mesh, OH-form, BIO-RAD-laboratory).

Eluant; water: flow rate: 0.37 ml./min.

(Analysis II)

Analytical column:

A column (15 cm × 8 mm I.D.) packed with Jeol Resin LCR-3 (Japan Electronics, sulfate-form ion exchange resin).

Eluant:

(i) 0.25 M borate buffer (pH 9.0); flow rate: 0.49 ml./min.; (ii) 0.15 M borate buffer (pH 7.7); flow rate: 0.49 ml./min. To detect the compounds giving negative orcin-sulfuric acid tests, the differential refractometer of Water Associates, for instance, was employed.

Gas chromatographic measurements were made using Hitachi Gas Chromatograph Model 063 (Hitachi, Ltd.) and Yanaco Gas chromatograph Model 5DH (Yanagimoto Co., Ltd.).

The samples were prepared as described below. A dry sample (a few mg.) containing the components of the validamycin complex was dissolved in dry pyridine (0.5 ml.) and, as an internal reference, melezitose (0.5 mg.) was added to the solution. Then, trimethyl-chlorosilane (0.5 ml.) and bis(trimethylsilyl)-acetimide (0.5 ml.) were further added. The mixture was allowed to react at 70° C for 20 minutes and the reaction product was injected into the gas chromatographic column.

As regards the column, good separations can be obtained if chromosolb W AW DMCS (Johns-Manville, Co.) or Chromosolb G AW DMCS (Johns-Manville, Co.), for instance, is used as the stationary phase and Silicone OV-1,OV-17 (1–5%) (Ohio Valley Speciality Chemical Co.), for instance, is used as the liquid phase in a glass column (1–2 m). The temperature of the column is maintained at 250°–300° C.

EXAMPLE 1

To an aqueous solution (adjusted to pH 7) containing 3% of glucose, 2.2% of raw soybean flour and 0.3% of peptone is added 0.4% of precipitated calcium carbonate, and 2 liters of the solution is dispensed into 4 flasks of 2 liters capacity, 500 ml. per flask. After sterilization, each of the flasks is inoculated with a loopful of *Streptomyces hygroscopicus* var. *limoneus* (ATCC No. 21431) from its slant culture. The flask is incubated on a reciprocating shaker at 28° C for 2 days to prepare a seed culture.

Separately, a stainless-steel tank of 200 liters capacity is charged with 100 liters of a medium (pH 7.0) composed of an aqueous solution containing 5% glucose, 3.6% raw soybean flour and 0.5% peptone, and 0.6% precipitated calcium carbonate. After sterilization, the tank is inoculated with 2 liters of the above seed culture and incubated for 114 hours. The procedure yields 68 liters of a culture filtrate containing 10,000 dilution units/ml. of the validamycin complex.

EXAMPLE 2

A culture (950-liters) of *Streptomyces hygroscopicus* var. *limoneus*, (ATCC:21431), which is obtainable by a procedure similar to that described in Example 1, is adjusted to pH about 4.0 with oxalic acid and, with the addition of a filtration aid, filtered. The resulting filtrate (720-liters) is passed through a column (resin: content 120-liters) of Amberlite (Rohm & Haas Company) IR-120 (OH-form). This column is washed with water (240-liters), then the washings are combined with the effluent. The pool is passed through a column (resin content: 140-liters) of Amberlite (same as above) IR-45 (OH-form) and, then, run onto a column (resin content: 60-liters) of Dowex (Dow Chemical Company) 50W × 2 (H-form). The latter column is washed with water and eluted with 0.5N-aqueous ammonia. The active fractions are pooled and concentrated under reduced pressure.

The concentrate (40-liters) is chromatographed using a column (resin content: 30-liters) of Amberlite IRA-900 (OH-form) and, as an eluant, water. Each fraction is assayed by thin-layer chromatography (silica gel G; developer: n-propanol-acetic acid-water:4/1/1), gas chromatography and liquid chromatography. The active compounds are eluted in the order of validoxylamines A and B, and validamycins D, C, F and E. Each fraction is concentrated to the consistency of a syrup, followed by the addition of acetone. The procedure yields 1.1 kg. of total of a crude powder of validamycin complex.

EXAMPLE 3

Each of the fractions containing validamycins C, D, E and F and validoxylamines A and B eluting from Amberlite IRA-900 in Example 2 is concentrated under reduced pressure to the consistency of a syrup, followed by the addition of acetone to precipitate the active components. The procedure yields 1.1 kg. of total of a crude powder of validamycin complex. In 2 liters of water is dissolved 400 g. of the above crude powder and the solution is chromatographed using a column (resin content: 22-liters) of Dowex 1 × 2 (OH-form) and, as an eluant, water. Each of the fractions is assayed by thin-layer chromatography and gas chromatography. Validoxylamines A, B and validamycin D are found in the 25 to 55-liter fractions, validamycin A in the 75 to 115-liter fractions, validamycins B and C in the 135 to 275-liter fractions and validamycins E and F in the 325 to 760-liter fractions. Each group of fractions is collected and concentrated under reduced pressure, followed by adding acetone to precipitate white powders. The procedure gives 42.8 g. of a white powder which is predominantly composed of validamicin D, 179.2 g. of a white powder composed predominantly of validamycin A, 42.0 g. of a white powder composed mainly of validamycins B and C, and 5.6 g. of a white powder mainly containing validamycins E and F.

EXAMPLE 4

Ten grams of the crude product relatively rich in validamycin D, which is obtainable according to Example 3, is chromatographed using a column (700 ml.) of Dowex 1 × 2 (OH-form, 100–200 mesh). The eluate is scanned with a differential refractometer and each of the fractions is identified and tested for purity by gas chromatography. It is found that validoxylamine A, in 0.8 to 2.0 liter fractions validoxylamine B and validamycin D occurs in the 1.6 to 2.0 liter fractions, respectively. The eluate containing validoxylamine A is concentrated to dryness under reduced pressure to obtain about 2.0 g. of a white powder. The eluate containing validamycin D and validoxylamine B are concentrated to dryness under reduced pressure to obtain about 4.6 g. of a white powder.

The above powder is dissolved in 0.1M-pyridine-acetate buffer (pH 6.0) and the solution is run onto a column (700 ml.) of Dowex 50W × 2 buffered with the same buffer as above. The column is eluted with a similar buffer, whereupon validoxylamine B and validamycin D are eluted in the 1.5 to 2.5 liter fractions and the 7.5 to 8.5 liter fractions, respectively. Each fraction is concentrated under reduced pressure and the concentrate is purified using a column (100 ml.) of Dowex 1 × 2 (OH-form) (eluant: water).

The eluate is concentrated under reduced pressure and the concentrate is added acetone to precipitate 0.7 g. of a white powder of validoxylamin B and 3.2 g. of a white powder composed of validamycin D.

To obtain a high purity grade of validamycin D, the crude product obtained is purified by chromatography on silica gel (Merck's silica gel 0.05–0.20 mm; n-propanolacetic acid-water:4/1/1) and Dowex 50W × 8 (eluant: 0.1M pyridine-acetate buffer, pH 6.0). Finally, the product is further purified with Dowex 1 × 2 (OH-form; eluant: water).

When hydrolyzed with acid, validamycin D yields 1 mole each of validoxylamine A and D-glucose.

EXAMPLE 5

Fifteen grams of the crude product relatively rich in validamycins B and C, which is obtainable according to Example 3, is chromatographed using a column (870 ml., 3.5 cm × 95 cm) of Dowex 1 × 2 (OH-form, 100–200 mesh) and, as an eluant, water. Each of the fractions is tested by thin-layer chromatography (silica gel G; n-propanol-acetic acid; water: 4/1/1; color reagent; naphthoresorcinol) or gas chromatography. Validamycin A (yield: about 5.0 g.) is eluted in the eluate corresponding to about 5 to 7 times of the volume of resin; validamycin C (yield: about 0.2 g.) in the eluate corresponding to about 10 to 20 times of the volume of resin; and validamycin B (yield: about 6.0 g.) in the eluate corresponding to about 12 to 18 times the volume of resin.

Since the crude powder obtained by the above-described procedure is predominantly composed of validamycin C but still contains a minor amount of validamycin B, it is further purified by the following procedure.

One (1.0) grams of the above powder is chromatographed using a column (1.3 cm × 90 mm; 200 ml.) of silica gel (Merck's silica gel, 0.05-0.2 mm) and, as a developer, n-propanol-acetic acid-water (4:1:1). Of the resulting fractions, those which give positive naphthoresorcinol reactions are confirmed by thin-layer chromatography. The fractions which contain validamycin C alone are collected and concentrated to dryness. The residue is further absorbed on Dowex 50W × 2(pyridine-form), which is eluted with 1N-pyridine-acetate buffer (pH 6.5). The fractions giving a positive naphthoresorcinol test are collected and concentrated to dryness under reduced pressure, whereupon a white powder of validamycin C is obtained. For the purpose of obtaining physicochemical data, the powder is further purified by means of a column of Dowex 1 × 2 (OH-form).

When hydrolyzed with acid, validamycin C yields 1 mole of validoxylamine and 2 moles of D-glucose.

EXAMPLE 6

The crude product (5.2 g.) obtained from the fractions comparatively rich in validamycins E and F, which are obtainable according to Example 3, is chromatographed using a column (2.7 cm × 43 cm) of Dowex 1 × 2 (OH-form, 100-200 mesh) and, as an eluant, water. The eluate is fractionated with a refractive index detector and each fraction is identified and tested for purity by means of automatic liquid chromatography and gas chromatography.

Validamycin B is eluted with distilled water in the eluate corresponding to about 20 times of the volume of the resin and validamycins E and F are obtained in the eluate corresponding to about 30 times of the volume of the resin.

In this procedure, validamycin F is eluated somewhat ahead of validamycin E and, as determined by automatic liquid chromatography, the first fractions contain comparatively large amounts of validamycin F and the later fractions rich in validamycin E. The fractions containing 80% or more validamicin E are concentrated to dryness under reduced pressure, whereupon 1.3 g. of a white powder is obtained.

The resulting powder containing 80% or more validamycin E is purified by chromatography on Dowex 50W × 8 (pyridine-form; eluant: 0.1M pyridine-acetate buffer, pH 6.0) and, then, on Dowex 1 × 2 (OH-form; eluant: water). The fractions containing validamycin E are collected and concentrated to dryness under reduced pressure. The procedure yields a white powder of validamycin E. When necessary, the above procedure is repeated once, whereupon a pure grade of validamycin E is obtained.

When hydrolyzed with acid, validamycin E yields 1 mole of validoxylamine and 2 moles of D-glucose.

In the same manner as described for validamycin E, the fractions rich in validamycin F are collected and purified to obtain a white powder of validamycin F. When necessary, the same procedure is repeated once, whereupon a pure grade of validamycin F is obtained.

When hydrolyzed with acid, validamycin F yields 1 mole of validoxylamine A and 2 moles of D-glucose.

Though validamycins E and F have similar physicochemical properties, a liquid chromatographic study reveals a significant difference between the two antibiotics; e.g. while validamycin F shows a retention time of 197 minutes, validamycin E shows a retention time of 233 minutes.

Incidentally, under the same conditions, validamycin C shows a retention time of 146 minutes.

EXAMPLE 7

To 150 mg. of the validamycin C obtained according to Example 5 are added 1 ml. of pyridine and 1 ml. of acetic anhydride, and the mixture is reacted and dissolved on a water bath under heating and stirring. The reaction mixture is allowed to stand at room temperature overnight, followed by the addition of water. The resulting precipitate is extracted with chloroform and the extract is washed with water. The chloroform is distilled off and water is added to the residue, whereupon 258 mg. of acetyl-validamycin C is obtained. $[\alpha]_D^{23} + 98.9°$ (C=1.0, CHCl$_3$);

Elementary analysis:

Found C, 51.45; H, 5.73; N, 1.04; Molecular weight: 1245 ± 50 (VPO**method, in ethyl acetate).

(VPO**: Vapour Pressure Osmometry)

The validamycin C acetate thus obtained (350 mg.) is dissolved in 3.5 ml. of methanol, and 20 ml. of sodium methylate (a solution of 0.5 g. sodium metal in 100 ml. methanol) is added. The mixture is allowed to stand at room temperature for 5 hours, at the end of which time it is run onto a column of Dowex 50W × 8 (H-form). The column is washed with water and, then, eluted with 1 N-HCl. The eluate is further chromatographed using a column of Dowex 1 × 2 (OH-form; eluant: water) and the active fractions are concentrated to dryness under reduced pressure to recover validamycin C.

EXAMPLE 8

To 400 mg. of the validamycin D obtained according to Example 4 are added 2.5 ml. of pyridine and 2 ml. of acetic anhydride, and the mixture is allowed to stand at room temperature overnight. It is treated in the same manner as Example 7 to obtain 690 mg. of acetyl-validamycin D. This product gives the following analytical data. $[\alpha]_D^{23} + 145°$ (C=1.0, CHCl$_3$);

Elementary analysis:

Found C, 52.86; H, 6.23; N, 1.44;

Molecular weight: 960 ± 50 (VPO method, in ethyl acetate).

At 0° C, 30 ml. of methanol saturated with ammonia is added to the above acetyl-validamycin D (550 mg.), and the mixture is allowed to stand at room temperature overnight. The reaction mixture is concentrated under reduced pressure and, then methanol is added to the residue. This procedure is repeated three times. The final residue is dissolved in water and purified by means of a column of Dowex 1 × 2 (OH-form), whereupon 228 mg. of validamycin D is obtained.

EXAMPLE 9

In N,N-dimethylformamide (5 ml.) is dissolved 1.37 g. of the crude product containing validoxylamine A (purity: about 80%) and the solution is refluxed with 10 ml. of acetone dimethyl ketal (2,2-dimethoxypropane) and 0.65 g. of p-toluenesulfonic acid in a water bath for 5 hours. The reaction mixture is allowed to cool and, then, the excess acetone dimethyl ketal is removed by distillation. The residue is dissolved in chloroform and, after washing with water, the chloroform layer is concentrated. The concentrate is purified by chromatography on silica gel (2 cm × 25 cm; eluant: chloroform) and the fractions are collected and concentrated. Then, ethanol is added to the concentrate to obtain crystals. m.p. 228°–231° C (decomp.); $[\alpha]_D^{23} + 97.0°$ (c=1.0, $CHCl_3$);

Elementary analysis

Found C, 62.56; H, 8.24; N, 2.83.

500 mg. of the isopropylidene-validoxylamine A thus obtained is refluxed together with 50 ml. of a 50% aqueous solution of acetic acid for about 5 hours until a clear solution is obtained. This solution is concentrated to dryness and, if required, purified by chromatography on Dowex 1 × 2 (OH-form). The product is finally crystallized from water-ethanol. Yield 285 mg.

What is claimed is:

1. A composition for controlling fungal plant diseases, which comprises (1) an effective fungal plant disease-controlling amount of at least one active ingredient selected from the group consisting of validamycin C, validamycin D, validamycin E, validamycin F and substantially non-phytotoxic acid salts of said validamycins, and (2) a non-phytotoxic carrier therefor.

2. A composition for controlling fungal plant diseases, which comprises an effective fungal plant disease-controlling amount of a combination of at least two active ingredients selected from the group consisting of validamycin C, validamycin D, validamycin E, validamycin F and substantially non-phytotoxic acid salts of said validamycins.

3. A composition as claimed in claim 1, wherein the active ingredient is validamycin C having the formula:

wherein R is O-α-D-glucopyranosyl-3-hydroxymethyl-4,5,6-trihydroxy-2-cyclohexenyl, and decomposing at 142° to 160° C.

4. A composition as claimed in claim 1, wherein the active ingredient is validamycin D having the formula:

wherein $R_1$ is O-α-D-glucopyranosyl-2,3,4-trihydroxy-5-hydroxymethyl-cyclohexyl.

5. A composition as claimed in claim 1, wherein the active ingredient is validamycin E having the formula:

wherein $R_2$ is O-α-D-glucopyranosyl-O-β-D-glucopyranosyl.

6. A composition as claimed in claim 1, wherein the active ingredient is validamycin F having the formula:

wherein $R_3$ is O-α-D-glucopyranosyl-3-hydroxymethyl-4,5,6-trihydroxy-2-cyclohexenyl, and decomposing at 165° to 173° C.

7. A composition as claimed in claim 1, wherein the active ingredient is a mixture of validamycins E and F.

8. A composition as claimed in claim 1, wherein the composition is in a liquid form and the content of the active ingredient is from about 0.0001% to about 0.5% by weight relative to the composition.

9. A composition as claimed in claim 1, wherein the composition is in a powder form and the content of the active ingredient is from about 0.01% to about 30% by weight relative to the composition.

10. A composition as claimed in claim 1, wherein the composition is in a concentrate form and the content of the active ingredient is from about 0.5% to about 80% by weight relative to the composition.

* * * * *